United States Patent
Birnkrant et al.

(10) Patent No.: US 8,029,440 B2
(45) Date of Patent: Oct. 4, 2011

(54) VIDEO BLADE LARYNGOSCOPE

(75) Inventors: Dashiell Birnkrant, Worcester, MA (US); James P. Barry, Charlton, MA (US)

(73) Assignee: Karl Storz Endovision, Inc., Charlton, MA (US)

( * ) Notice: Subject to any disclaimer, the term of this patent is extended or adjusted under 35 U.S.C. 154(b) by 302 days.

(21) Appl. No.: 11/696,524

(22) Filed: Apr. 4, 2007

(65) Prior Publication Data
US 2008/0249370 A1 Oct. 9, 2008

(51) Int. Cl.
*A61B 1/267* (2006.01)
(52) U.S. Cl. .......................... 600/188; 600/112
(58) Field of Classification Search .................. 600/169, 600/184, 185–200, 112
See application file for complete search history.

(56) References Cited

U.S. PATENT DOCUMENTS

| | | | | |
|---|---|---|---|---|
| 4,279,246 A * | 7/1981 | Chikama | .................. | 600/169 |
| 4,807,594 A * | 2/1989 | Chatenever | .................. | 600/112 |
| 5,647,840 A * | 7/1997 | D'Amelio et al. | .................. | 600/169 |
| 5,800,344 A * | 9/1998 | Wood et al. | .................. | 600/188 |
| 6,013,081 A * | 1/2000 | Burkinshaw et al. | .................. | 606/88 |
| 6,083,151 A * | 7/2000 | Renner et al. | .................. | 600/114 |
| 6,106,457 A * | 8/2000 | Perkins et al. | .................. | 600/175 |
| 6,296,528 B1 * | 10/2001 | Roberts et al. | .................. | 439/676 |
| 6,386,452 B1 * | 5/2002 | Kawamura | .................. | 235/454 |
| 6,413,209 B1 * | 7/2002 | Thompson | .................. | 600/169 |
| 6,543,447 B2 | 4/2003 | Pacey | | |
| 6,655,377 B2 | 12/2003 | Pacey | | |
| 6,676,598 B2 * | 1/2004 | Rudischhauser et al. | ..... | 600/188 |
| 6,840,903 B2 * | 1/2005 | Mazzei et al. | .................. | 600/188 |
| 6,875,169 B2 * | 4/2005 | Berci et al. | .................. | 600/112 |
| 2003/0088156 A1 * | 5/2003 | Berci et al. | .................. | 600/188 |
| 2003/0195390 A1 * | 10/2003 | Graumann | .................. | 600/188 |
| 2004/0133073 A1 * | 7/2004 | Berci et al. | .................. | 600/112 |
| 2005/0148364 A1 * | 7/2005 | Yamashita | .................. | 455/557 |
| 2005/0148821 A1 * | 7/2005 | Berci et al. | .................. | 600/188 |
| 2005/0192481 A1 | 9/2005 | Berci et al. | | |
| 2006/0069314 A1 * | 3/2006 | Farr | .................. | 600/179 |

FOREIGN PATENT DOCUMENTS

| | | |
|---|---|---|
| EP | 1847214 A2 | 10/2007 |
| JP | 2004309719 A | 11/2004 |
| WO | 9846121 A1 | 10/1998 |
| WO | 2004035106 A2 | 4/2004 |

OTHER PUBLICATIONS http://www.mercksource.com/pp/us/cns/cns_hl_dorlands_split.jsp?pg=/ppdocs/us/common/dorlands/dorland/two/000016045.htm, Nov. 4, 2009.*
Partial European Search Report, EP08006215, Jul. 25, 2008, 2 pages.

* cited by examiner

*Primary Examiner* — Thomas C Barrett
*Assistant Examiner* — Christian Sevilla
(74) *Attorney, Agent, or Firm* — St. Onge Steward Johnston & Reens LLC

(57) ABSTRACT

A laryngoscope including a control circuit and a camera having a housing enclosing the camera that is detachably connectable to a handle, where the camera functions and is compatible with a wide variety of displays. The laryngoscope may optionally be used in either the video mode where the user views a display presenting image data of the area ahead of the blade, or the user may use the laryngoscope in the direct visualization where the user uses the laryngoscope in a traditional manner directly viewing the area ahead of the blade during the intubation procedure. When used in the video mode, an LED is positioned adjacent to a window enclosing the digital image sensor to defog the window.

17 Claims, 7 Drawing Sheets

VIDEO BLADE LARYNGOSCOPE

FIELD OF THE INVENTION

The invention relates to a laryngoscope, and more particularly to a laryngoscope that may be used with many differing video monitors and that also may be used as either a video laryngoscope or as a direct visualization laryngoscope having a blade with a smooth upper surface so as not to interfere with direct visualization of a patient's trachea.

BACKGROUND OF THE INVENTION

A number of medical procedures require ventilation be provided to the patient, which may be provided through an endotracheal tube. This tube may be inserted into the trachea. It should be noted that when the tube is inserted, the patient is asleep hyperoxygenated and then paralyzed for the procedure, and therefore not breathing. As the ventilator is not yet in operation, the physician must work quickly to insert the endotracheal tube.

With the advent of endoscopic equipment and small cameras, instrumentation can enable viewing of the cords and larynx on a video screen facilitating the intubation of the patient in a relatively quick and safe manner. In some instances it has been determined that direct visualization of the cords and larynx is preferred over the video method. However, video laryngoscopes due to their specialized construction, traditionally do not allowed for intubation by direct visualization. Rather, a physician must discard the video laryngoscope and obtain a traditional non-video laryngoscope to perform this procedure. This disadvantageously leads to delay in intubation of the patient due at least in part to the fact that the physician has to change instruments. It is highly desirable to reduce any cause for delay in the intubation process.

U.S. Pat. Nos. 6,655,377 ("the '377 patent") and 6,543,447 ("the '447 patent") disclose video laryngoscopes having a lifter portion that is long enough to extend into the laryngopharynx and operably engage the epiglottis of the patient. One function of the lifter portion is to hold the intubation tube with the video device is positioned on a lower side of the blade opposite to the lifter portion. While this configuration functions as a video laryngoscope, the lifter portion extends upward from the upper surface of the blade such that any direct visualization by a physician is virtually impossible. As such, a physician would have to discard and retrieve a separate laryngoscope to perform this procedure.

Another problem that traditional video laryngoscopes face is the limited interface ability they have with monitors. For example, a video laryngoscope typically is designed and can only be used with a single type of monitor, e.g. either an O.R. monitor or a P.C. This is disadvantageous as the physician may desire to switch monitors, for example, the laryngoscope may be attached to an O.R. monitor but the physician wants to connect the laryngoscope to a relatively small portable computer monitor as the patient is transported. The laryngoscope would then have to be replaced with a device capable of functioning with a P.C. monitor.

Yet another problem associated with video laryngoscopes is the fact that, many imaging chips are positioned in a cavity or enclosure at a distal end of the laryngoscope blade and are enclosed by a transparent window. However, the window often becomes fogged during the procedure thereby limiting the ability of the physician to see clearly.

SUMMARY OF THE INVENTION

It is therefore desired to provide a video laryngoscope that may be used either as a video laryngoscope or as a direct visualization laryngoscope for intubation of a patient.

It is also desired to provide a video laryngoscope that is capable of functioning with many differing monitors.

It is further desired to provide a video laryngoscope that is compatible with many differing signal formats.

It is still further desired to provide a video laryngoscope that provides for de-fogging to maintain clear visualization for the physician.

These and other objectives are achieved by providing a laryngoscope that utilizes a blade having a smooth upper surface so as not to interfere with the physician's direct visualization of the areas in and around the laryngopharynx during intubation. The laryngoscope is provided with a digital imaging chip and an illumination device, e.g. a Light Emitting Diode (LED) for illumination of an area to be viewed. It is contemplated that the digital imaging chip may comprise, for example, either a CCD, a C-Mos chip, or the like capable of, for instance, generating image data from processing reflected light picked up from an area to be viewed and/or from processing digital images from a camera in order to further improve the quality of the digital images.

Further, it is contemplated that the digital imaging chip may be provided as a "hard-wired" or as a "wireless" device for transmitting image data picked up from the area to be viewed.

In one advantageous embodiment, a digital imaging chip and an LED are positioned in an enclosure that may be detachably connectable to, for example, the laryngoscope blade. The enclosure is provided with an elongated case and be provided with a coupling mechanism for coupling the enclosure to the handle and/or blade. In one embodiment, the imaging chip and the LED are provided at a distal end of the enclosure, while the coupling mechanism is provided at the opposite proximal end of the enclosure such that electrical connections may be provided for the imaging chip and the LED. In this manner, electrical power may be transmitted to the LED to illuminate the area ahead of the blade, while the digital imaging chip may generate and transmit image data back to imaging circuitry positioned in the handle. It is further provided that the LED may be provided as a relatively high-powered LED and is used to heat a window at the distal end of the enclosure such that the window is maintained free of fogging. The LED may be run, for example, at half power.

In addition, the enclosure may be positioned in a channel provided in the blade to securely hold the enclosure.

In another advantageous embodiment, a universal control circuit, such as a camera, may be positioned in the handle of the laryngoscope. The universal camera may be removable and may include a connector to couple to the handle, or may include a connector that couples directly to the enclosure. The universal camera may include many differing configurations including, for example but not limited to, a USB version 2.0 for connection to a Windows XP device over a USB 2.0 cable, a composite video version for connection to a NTSC over a composite video cable, a UWB wireless video version (USB) using a USB 2.0 signal, and/or a UWB wireless video version using an NSTC signal to name a few.

In this manner, any sensitive electronics may be removed from the handle, for example, during the sterilization process so that they are not exposed to the relatively high temperatures encountered during the process.

The blade of the laryngoscope is advantageously provided with a smooth upper surface such that the physician may use the laryngoscope either in the "video mode" or in may intubate a patient by direct visualization as desired. It is further contemplated that a plurality of blades may be detachably connectable to the handle, while the enclosure is detachably connectable to the blade and/or handle.

While it is preferred to locate the digital imaging device and the LED in the enclosure that is attachable to the blade, it is contemplated that one or both of the digital imaging device and/or the LED may be positioned in the removable universal camera, which may, for example, be a digital camera having a dedicated digital imaging chip.

It is still further contemplated that the laryngoscope may be provided with a direct wired connection to, for example, a video monitor, or may be provided with a wireless connection to the display equipment, which may comprise use of Ultra Wide Band (UWB) technology.

Accordingly, in one advantageous embodiment a laryngoscope system is provided comprising a handle having a cavity located therein, the cavity having a connector, a blade coupled to the handle and a camera detachably connectable to the connector. The laryngoscope system also comprises a sleeve coupled to the camera, an illuminating device for providing illuminating light to an area in front of the distal end of the blade and a digital imaging device for generating image data of the area in front of the distal end of the blade. In addition, the laryngoscope system includes a display coupled to the camera, the display receiving and displaying the image data.

In another advantageous embodiment a method for intubating a patient with a laryngoscope is provided comprising the steps of coupling a camera to a connector located in a cavity in a handle, coupling a blade to the handle and coupling a sleeve to the camera. The method includes the steps of transmitting illuminating light to an area in front of the distal end of the blade, generating image data of the area in front of the distal end of the blade and transmitting the image data to the camera. The method further includes the steps of coupling a display to the control circuit camera, transmitting the image data to the display and displaying the image data on a display.

Other objects of the invention and its particular features and advantages will become more apparent from consideration of the following drawings and accompanying detailed description.

DETAILED DESCRIPTION OF THE INVENTION

Figure 1:
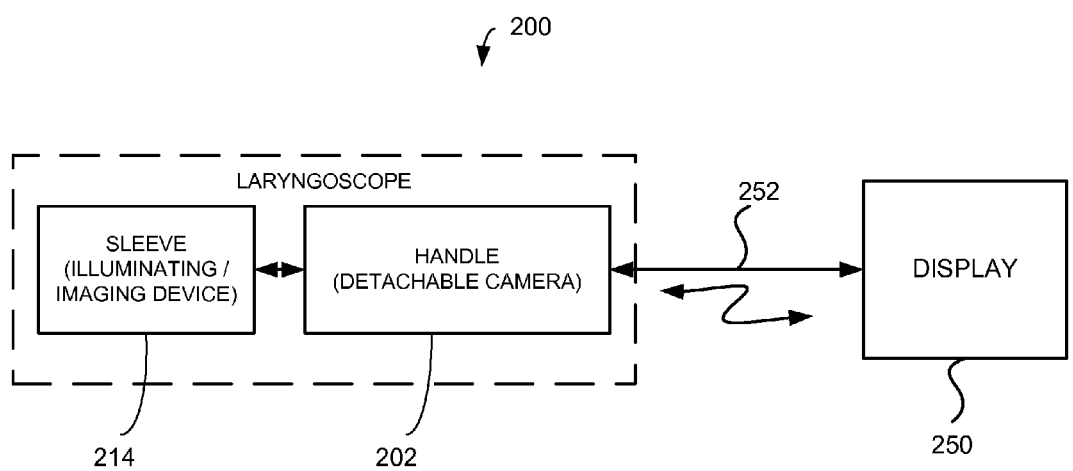
FIG. 1 is a block diagram of one advantageous embodiment of the present invention.

Referring now to the drawings, wherein like reference numerals designate corresponding structure throughout the views.

Figure 2:
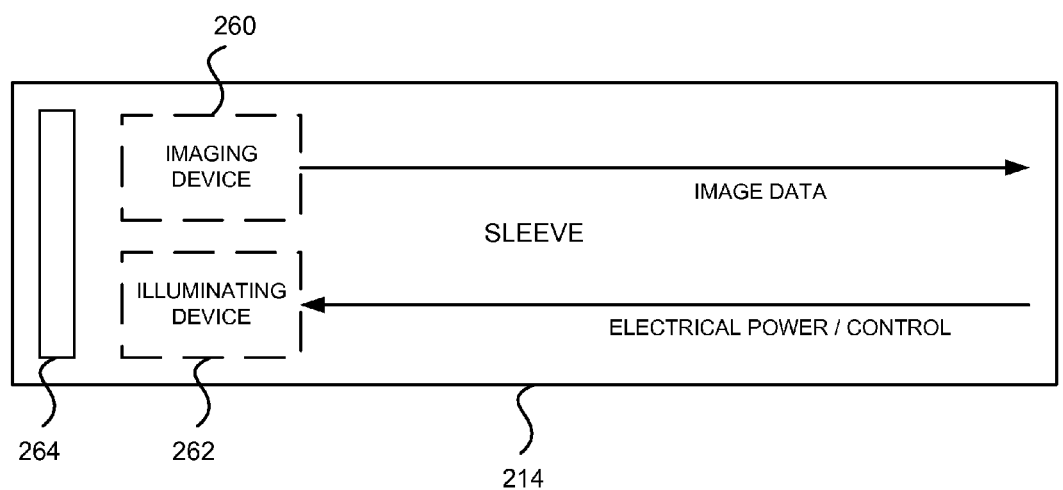
FIG. 2 is a block diagram of sleeve according to FIG. 1.
Figure 3:
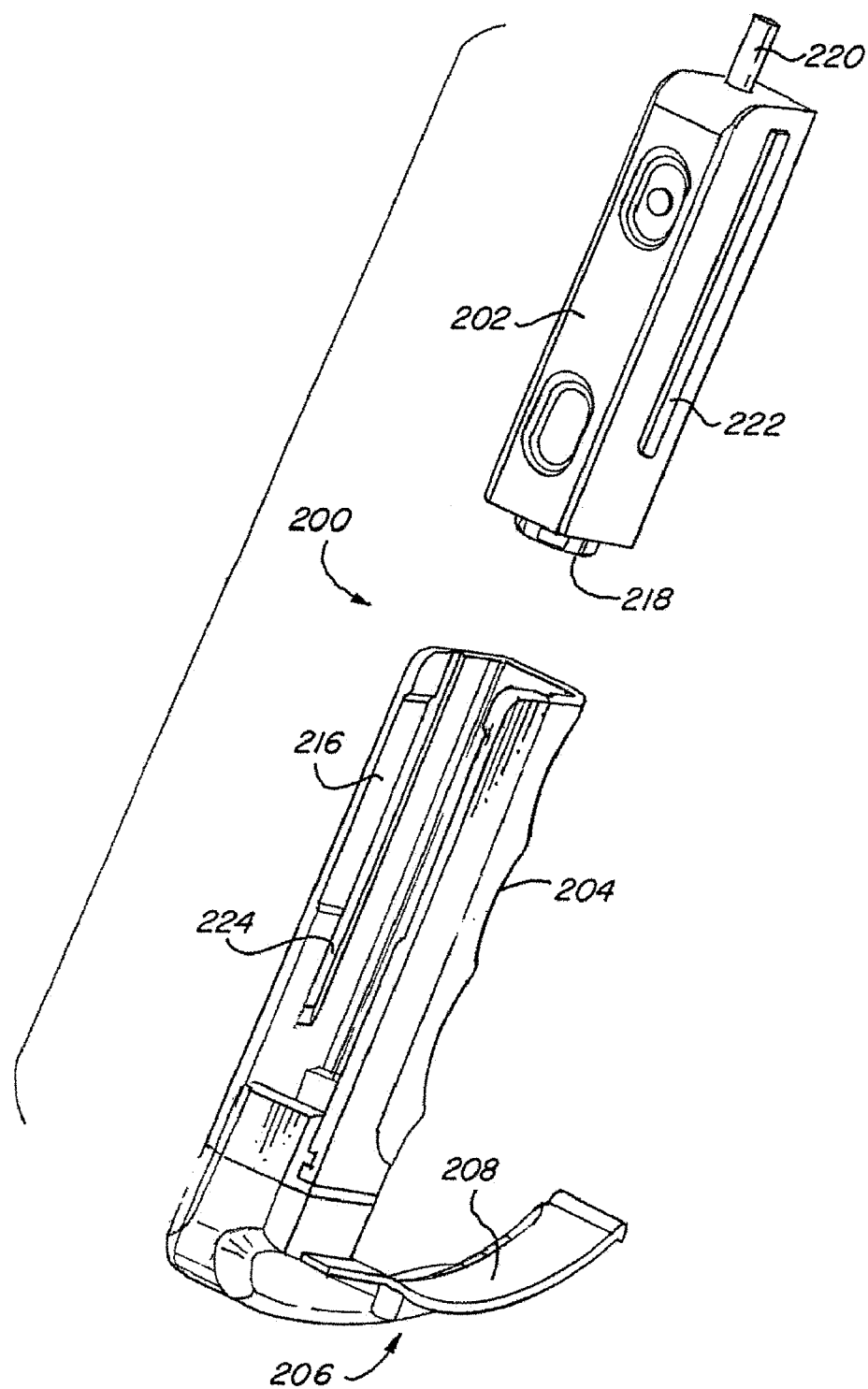
FIG. 3 is a perspective view of the embodiment according to FIG. 1.

One advantageous embodiment of the present invention is variously illustrated in FIGS. 1-7 including laryngoscope 200. FIGS. 1 and 2 are block diagrams illustrating various functional arrangements of laryngoscope 200, while FIGS. 3-7 are various prospective views of an advantageous embodiment of the present invention.

Laryngoscope 200 generally comprises a camera 202, which is insertable into or detachably connectable to a handle 204 of the laryngoscope 200. In addition, a blade 206 is coupled to handle 204 and a sleeve 214 may be coupled to camera 202 for transmitting image data to the camera, which is in turn, transmitted to a display 250. FIG. 1 illustrates use of, for example, a cable 252 or use of a wireless coupling to display 250.

It is contemplated that cable 252 may provide electrical power to camera 202 and may also transmit image data to display 250. However, in a wireless embodiment, a battery may be located in handle 204.

Referring to FIG. 2, an imaging device 260 and an illumination device 262 are each positioned at a distal end of sleeve 214. Also illustrated is window 264. Illumination device 262 may comprise, for example, an LED positioned adjacent to window 264. Illumination device 262 is provided for illumination of an area to be viewed, such as, for example, an area ahead of the distal end of blade 206. It is contemplated that illumination device 262 may operate in a fully ON state when laryngoscope 200 is in use, or may, in one advantageous embodiment, be pulsed in sync with imaging device 260. In addition, the LED may be used to de-fog window 264. In one embodiment, the LED provided as a relatively high-powered LED and run at half power or more providing both illumination and heating of the window 264 to provide a de-fogging function.

In a battery-powered version, the battery may comprise any battery type as is commonly used in industry and is contemplated that it may have a twelve-hour battery life. Further, the battery may in one advantageous embodiment be rechargeable.

Imaging device 260 may pick up reflected light from an area to be viewed and translates the reflected light into image data that is transmitted for display on display 250. This transmission may advantageously comprise a hard-wired connection or may be wireless. For hard-wired connections, the cable may comprise an electrical connection providing power to camera 202 and image data to display 250. It is further contemplated that data signals, control signals and power may all be transmitted over a signal channel thereby minimizing the size of the interconnecting cables.

For wireless transmission, any acceptable transmission means may be used including but not limited to, for example, radio-frequency transmission or the like. In one embodiment, transmission circuitry is positioned in handle 204 for transmission of the image data to display 250.

The coupling between laryngoscope 200 and display 250 is illustrated in FIG. 1 as either a curved line with arrows in two different directions (wireless) or the straight line with arrows in two different directions (hard-wired). Display 250 may comprise virtually any commercially available video system and monitor for display of the image data generated by imaging device 260.

In an advantageous embodiment, wireless transmission may comprise an UWB transmission. As UWB systems transmit signals across a much wider frequency than conventional systems, a relatively large amount of data may be transmitted. This is advantageous for video medical systems, where relatively high resolution is beneficial and signal lag is undesirable. A number of UWB technologies may effectively be used including, for example, Multiband Orthogonal Frequency Division Modulation (OFDM) or Direct Sequence Ultra-Wideband (DS-UWB).

It is contemplated that imaging device 260 may comprise, in one advantageous embodiment, a CMOS chip (e.g. OmniVision's OV7660 VGA CMOS electronic camera sensor). The CMOS chip may be made relatively small in size, utilizes very little power and is inexpensive to manufacture and may be connected to any necessary drive electronics using a flex circuit. In addition, the signal format may be selected to utilize nonsinusoidal signals, which will not interfere with the sinewave spectrum so as to minimize any interference in existing operating room equipment. This advantage may be is achieved, at least in part because the transmitted power may be spread over a relatively large bandwidth such that the amount of power at any one frequency band at any time is relatively small.

Figure 4:
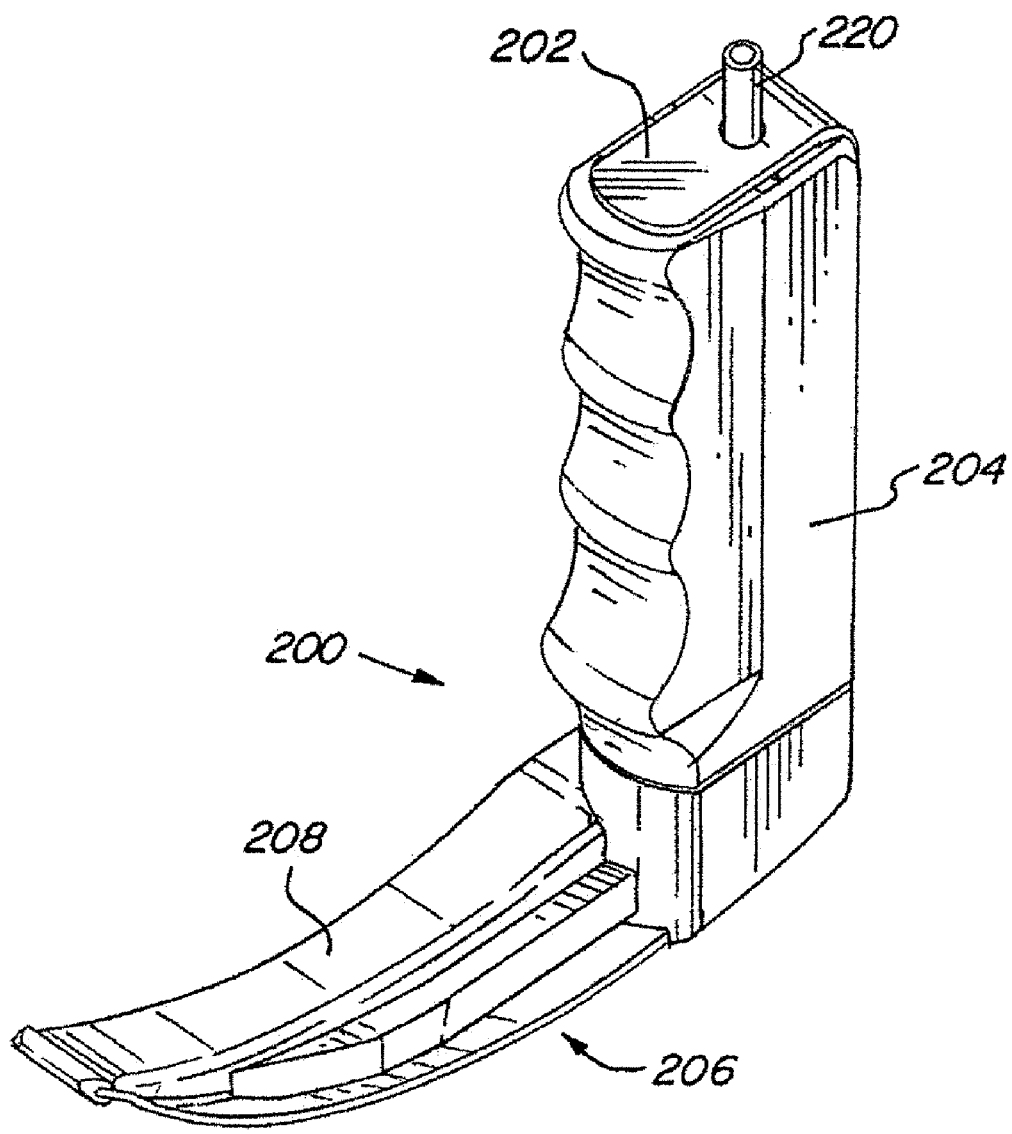
FIG. 4 is another perspective view of the embodiment according to FIG. 1.

In one advantageous embodiment, blade 206 is detachably connectable to handle 204. Advantageously, blade 206 is provided slightly curved upward as a traditional Macintosh style blade, but could be provided relatively straight as per the traditional Foregger-Magill blade. As can be seen in FIG. 4, blade 206 is advantageously provided with a relatively smooth upper surface 208, which in part, allows the physician to use laryngoscope 200 either in the video mode (e.g. viewing a video screen during the intubation process) or via direct visualization. It is contemplated that in one embodiment, blade 206 may be provided as a rigid material, such as a metal or an alloy, but is not limited to these material compositions.

Figure 5:
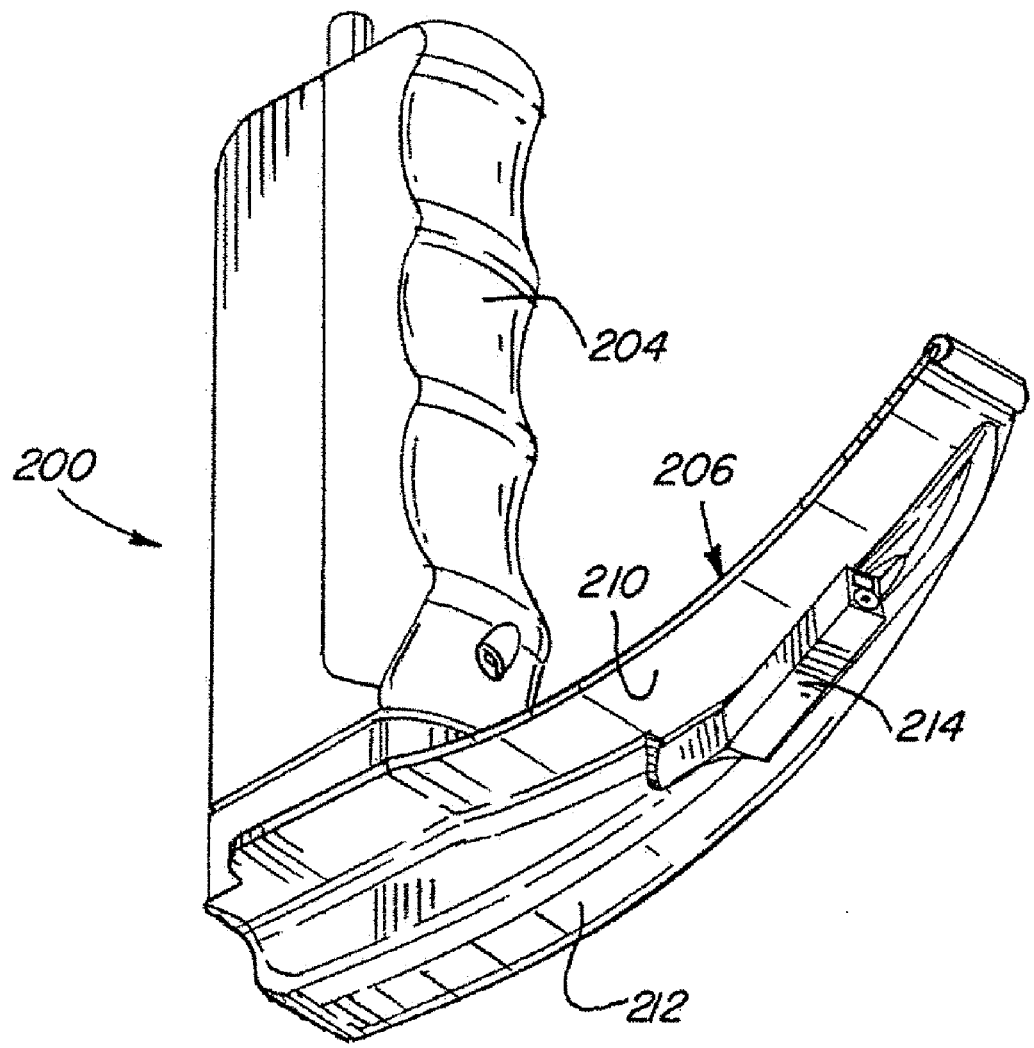
FIG. 5 is still another perspective view of the embodiment according to FIG. 1.
Figure 6:
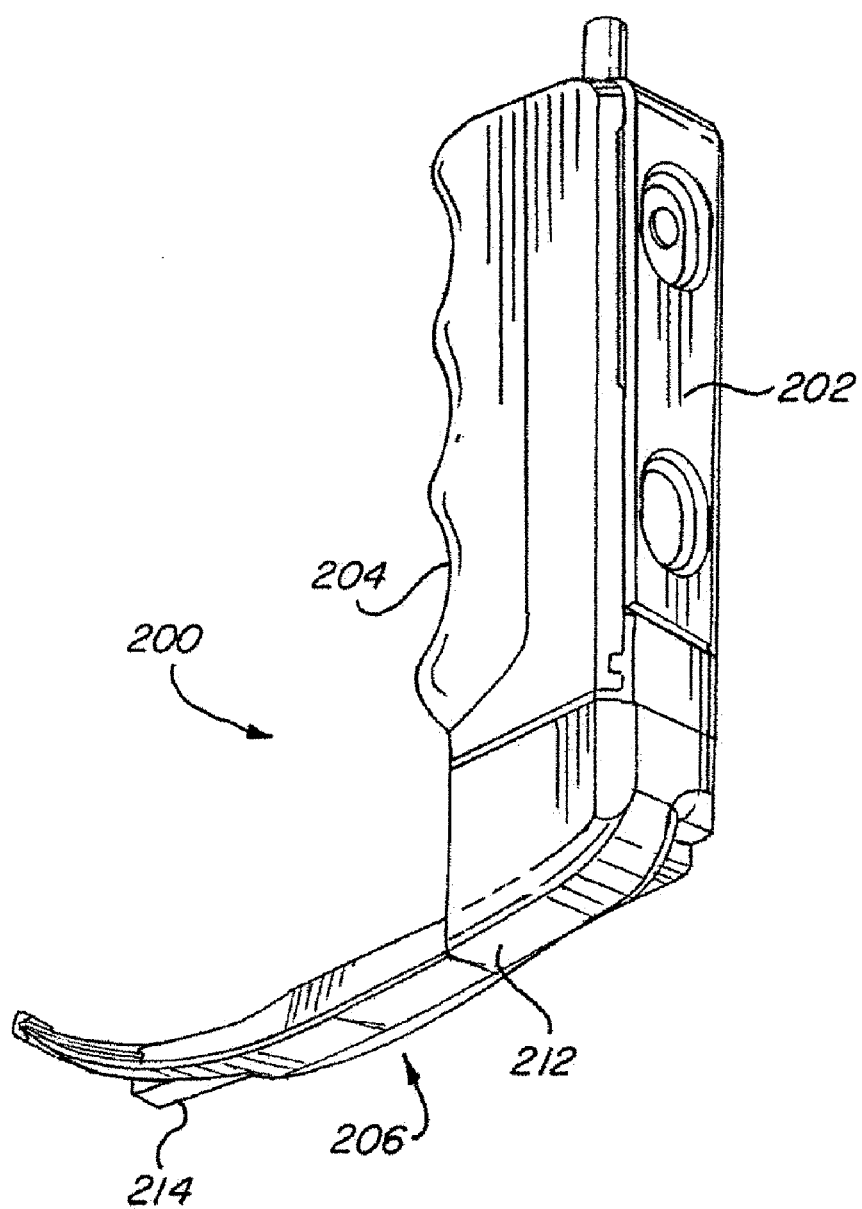
FIG. 6 is yet another perspective view of the embodiment according to FIG. 1.
Figure 7:
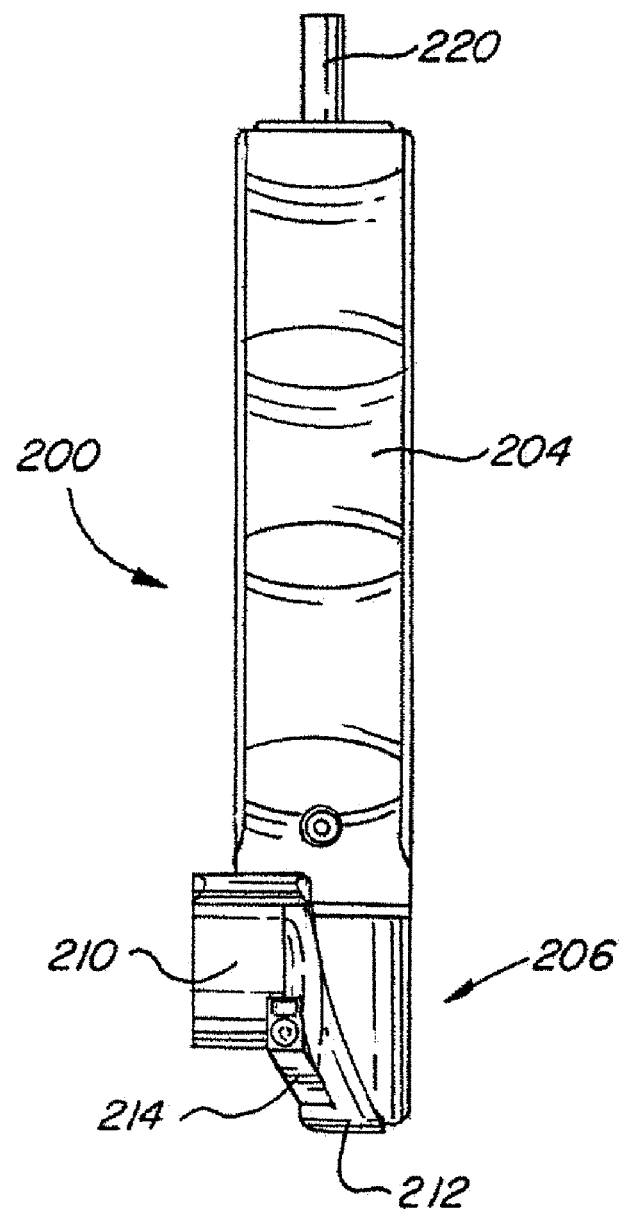
FIG. 7 is still another perspective view of the embodiment according to FIG. 1.

As seen in FIGS. 5 and 6, blade 206 is provided with a stepped portion 210 such that a cavity is formed in the lower portion 212 of blade 206 for receiving sleeve 214, which may be detachably connectable to blade 206. As in the previously described embodiments, the illumination may be provided by an LED, which in this embodiment, is positioned in sleeve 214. In addition, the imaging device may also be positioned in sleeve 214 and may comprise a digital imaging device such as a CMOS device or chip.

As seen in FIG. 1, camera 202 is insertable into a cavity 216 of handle 204 and lies essentially flush with handle 204 with fully inserted (FIG. 4). It is contemplated that the device may provide an audible "click" when camera 202 is fully inserted into cavity 216 providing an audible indication to the user that the coupling of camera 202 to handle 204 is complete. It is further contemplated that a lock, such as an interference fitting between camera 202 and cavity 216, may be provided to maintain camera 202 securely coupled to handle 204 during use. Also provided on the exterior surface of camera 202 is protrusion 222, which is provided as a ridge running along a longitudinal length of camera 202. Protrusion 222 is provided to engage with a channel 224 located in cavity 216. In this manner, the camera 202 may only be removed from cavity 216 by longitudinally sliding the camera 202 out of cavity 216.

A coupler 218 is provided at the insertion end of camera 202, which is designed to engage with a complementary connector (not shown) positioned inside cavity 216 of handle 204. Depending upon the application, the coupler may couple, electrical cables/channels, optical cables/channels and/or combinations thereof. In addition, cable 220 may be provided to channel electrical signals, optical signals/energy and/or combinations thereof between camera 202 and the video system (Display).

Although the invention has been described with reference to a particular arrangement of parts, features and the like, these are not intended to exhaust all possible arrangements or features, and indeed many other modifications and variations will be ascertainable to those of skill in the art.

What is claimed is:

1. A laryngoscope system comprising:
   a handle having a cavity located therein with a connector positioned in the cavity;
   a blade coupled to said handle;
   a camera having a housing that encloses said camera, said camera having a coupler being detachably engageable to the connector and said camera housing is positioned within said cavity when said camera is connected to the connector;
   a sleeve coupled to said camera;
   an illuminating device for providing illuminating light to an area in front of the distal end of said blade;
   a digital imaging device for generating image data of the area in front of the distal end of said blade;
   a display coupled to said camera, said display receiving and displaying the image data wherein said connector comprises an electrical channel for transmitting electrical power to said illuminating device.

2. The laryngoscope system according to claim 1 wherein said connector further comprising a data channel for transmitting image data from said digital imaging device.

3. The laryngoscope system according to claim 1 wherein said blade comprises a smooth upper surface so as not to interfere with direct visualization by a user of an area in front of a distal end of the blade during intubation such that a user may intubate a patient with the laryngoscope system either by direct visualization of the area ahead of the blade or by viewing the image data on said display.

4. The laryngoscope system according to claim 1 wherein said digital imaging device is positioned in said sleeve.

5. The laryngoscope system according to claim 1 wherein said illuminating device is positioned in said sleeve.

6. The laryngoscope system according to claim 1 further comprising a cable coupling said digital imaging device to said display.

7. The laryngoscope system according to claim 6 wherein said cable comprises a USB cable.

8. The laryngoscope system according to claim 1 wherein said illuminating device comprises an LED.

9. The laryngoscope system according to claim 8 wherein the LED is pulsed in sync with a shutter of said digital imaging device.

10. The laryngoscope system according to claim 8 further comprising a window positioned at a distal end of said sleeve and said LED is positioned adjacent to said window to heat and defog the window.

11. The laryngoscope system according to claim 1 wherein said blade is detachably coupled to said handle.

12. The laryngoscope system according to claim 1 wherein upon connection to a display, said camera identifies said connected display and provides an image data stream compatible with the connected display.

13. The laryngoscope system according to claim 12 wherein said camera includes signal configurations selected from the group consisting of: USB connection over a USB cable, a composite video connection to a NTSC over a composite video cable, a UWB wireless video connection using a USB signal, a UWB wireless video connection using an NSTC signal and combinations thereof.

14. The laryngoscope system according to claim 1 wherein said sleeve is detachably coupled to said camera.

15. The laryngoscope system according to claim 1 said camera is provided with a keyed outer surface that engages with an interior surface of said cavity.

16. The laryngoscope system according to claim 15 wherein said keyed outer surface comprises at least one protrusion that engages with a channel located in the interior surface of said cavity such that said camera may be longitudinally slid into said cavity.

17. The laryngoscope system according to claim 1 wherein when said camera engages with said connector, there is an audible indication that the camera is fully inserted into said cavity.

* * * * *